Figure 1:
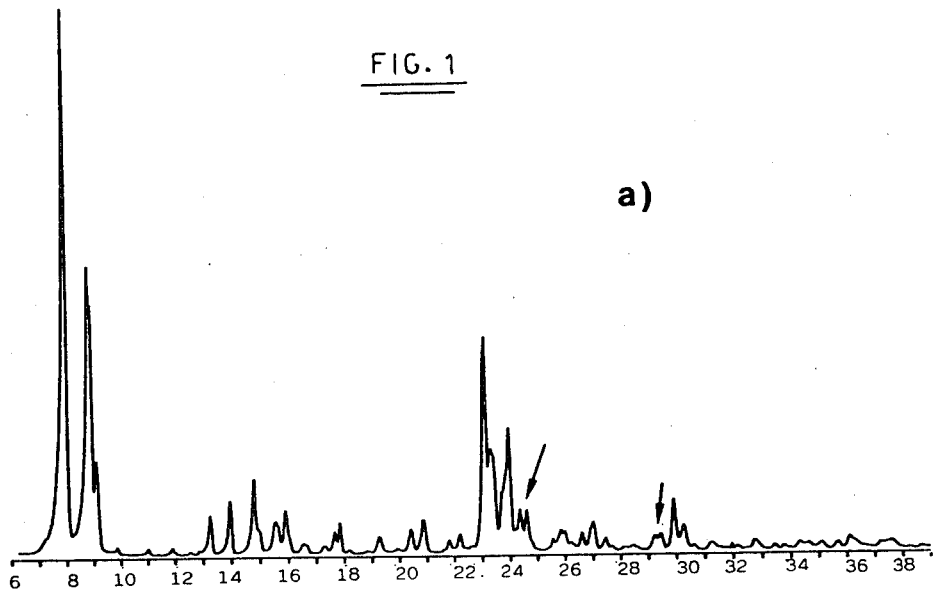
Figure 1:
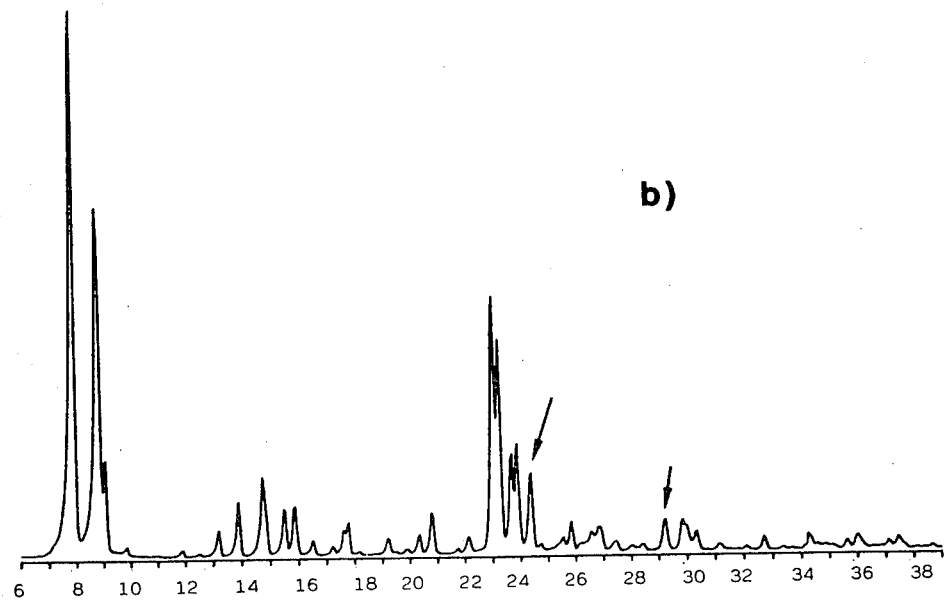

United States Patent [19]

Esposito et al.

[11] Patent Number: 4,480,135
[45] Date of Patent: Oct. 30, 1984

[54] PROCESS FOR OXIDIZING ALCOHOLS TO ALDEHYDES AND/OR KETONES

[75] Inventors: Antonio Esposito; Carlo Neri; Franco Buonomo, all of S. Donato Milanese, Italy

[73] Assignee: Anic S.p.A., Palermo, Italy

[21] Appl. No.: 513,801

[22] Filed: Jul. 14, 1983

[30] Foreign Application Priority Data

Jul. 28, 1982 [IT] Italy ................................ 22607 A/82

[51] Int. Cl.$^3$ ............................................. C07C 45/29
[52] U.S. Cl. ................................... 568/385; 568/311; 568/342; 568/485; 568/487; 568/430
[58] Field of Search ............... 568/311, 385, 430, 485, 568/487, 342

[56] References Cited

U.S. PATENT DOCUMENTS 3,531,519  9/1970  Perkin et al. ......................... 568/311
4,086,261  4/1978  Mitchell et al. ..................... 568/485
4,310,704  1/1982  Mimoun et al. ...................... 568/385

FOREIGN PATENT DOCUMENTS 55-102527  8/1980  Japan .................................... 568/385

Primary Examiner—James H. Reamer
Attorney, Agent, or Firm—Hedman, Gibson, Costigan & Hoare

[57] ABSTRACT

A process for oxidizing primary and/or secondary alcohols to the corresponding aldehyde and/or ketone derivatives, consisting of reacting said alcohols with an aqueous solution of hydrogen peroxide in the presence of synthetic zeolites containing titanium atoms, of general formula:

$$x\text{TiO}_2.(1-x)\text{SiO}_2,$$

where x lies between 0.0001 and 0.04, and possibly in the presence of one or more solvents, operating at a temperature of between 20° and 100° C.

10 Claims, 2 Drawing Figures a)

b)

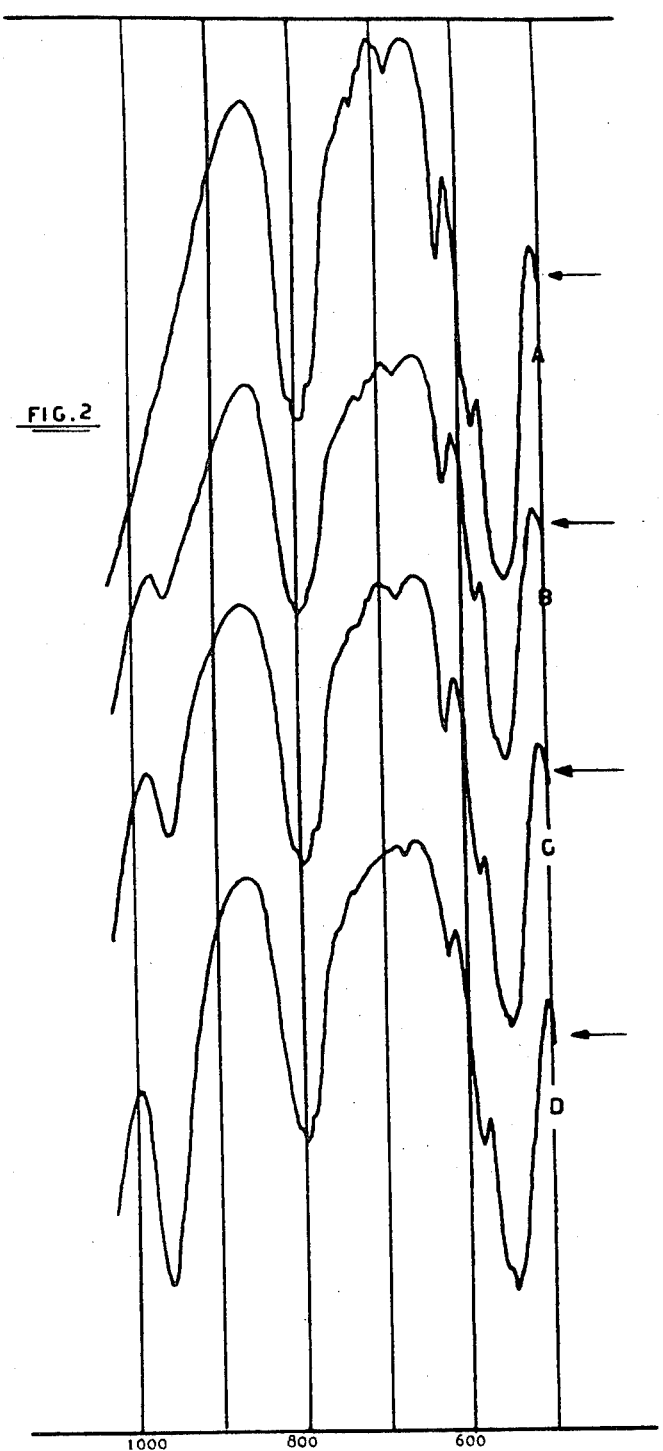

PROCESS FOR OXIDIZING ALCOHOLS TO ALDEHYDES AND/OR KETONES

This invention relates to a process for oxidising primary and/or secondary alcohols to the corresponding aldehyde and/or ketone derivatives by means of hydrogen peroxide, using a synthetic zeolite as catalyst. Various processes for the stoichiometric oxidation of primary and secondary alcohols are known, using metal salts or metal oxides as catalyst.

The metal salts mostly used for these reactions are platinum, palladium, ruthenium, cooper and cobalt salts to which an oxidising agent is added, this being either hydrogen peroxide (for Pt and Pd) or oxygen (for Ru, Cu and Co). The metal oxides mostly used are $V_2O_5$, $RuO_4$ and $CrO_3$. However, the aldehydes and ketones obtained from alcohols by using the aforesaid catalysts have the drawback of oxidising rapidly to the corresponding carboxylic acids. We have now surprisingly found that a synthetic zeolite containing titanium atoms is able to selectively oxidise primary and secondary alcohols to the corresponding aldehyde and ketone derivatives by means of $H_2O_2$, without the aldehydes and ketones subsequently oxidising to the corresponding carboxylic acids.

The subject matter of the present invention is a process for oxidising primary and/or secondary alcohols to the corresponding aldehyde and/or ketone derivatives, consisting of reacting said alcohols with an aqueous solution of hydrogen peroxide in the presence of synthetic zeolites containing titanium atoms (titanium silicalites), of general formula:

$$xTiO_2 \cdot (1-x)SiO_2,$$

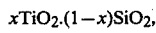

where x lies between 0.0001 and 0.04, and possibly in the presence of one or more solvents.

The synthetic zeolites used for the epoxidation reaction are described in Belgian Pat. No. 886,812, of which we repeat some points illustrating the material and relative method of preparation. The composition range of the titanium silicalite expressed in terms of molar ratios of the reagents is as follows:

| Molar ratio of reagents | | preferably |
|---|---|---|
| $SiO_2/TiO_2$ | 5–200 | 35–65 |
| $OH^-/SiO_2$ | 0.1–1.0 | 0.3–0.6 |
| $H_2O/SiO_2$ | 20–200 | 60–100 |
| $Me/SiO_2$ | 0.0–0.5 | 0 |
| $RN^+/SiO_2$ | 0.1–2.0 | 0.4–1.0 |

$RN^+$ indicates the nitrogenated organic cation deriving from the organic base for the preparation of the titanium silicalite (TS-1).
Me is an alkaline ion, preferably Na or K.

The final TS-1 has a composition satisfying the formula $$xTiO_2 \cdot (1-x)SiO_2,$$

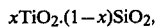

where x lies between 0.0001 and 0.04, and preferably between 0.01 and 0.025. The TS-1 is of the silicalite type, and all the titanium substitutes the silicon. The synthetic material has characteristics which are shown up by X-ray and infrared examination.

The X-ray examination is carried out by means of a powder diffractometer provided with an electronic pulse counting system, using the radiation $CuK\alpha^-$. The titanium silicalites (TS-1) are characterised by a X-ray diffraction spectrum as shown in FIG. 1b. This spectrum is similar overall to the typical spectrum of silicalite (FIG. 1a), however it has certain clearly "single" reflections where double reflections are evident in the pure silicalite spectrum. Because the spectral differences between TS-1 and silicalite are relatively small, special accuracy is required in the spectral determination. For this reason TS-1 and silicalite were examined by the same apparatus, using $Al_2O_3$ as the internal standard.

Table 1 shows the most significant spectral data of a TS-1 where x=0.017, and of a pure silicalite. The constants of the elementary crystalline cell were determined by the minimum square method, on the basis of the interplanar distances of 7–8 single reflections lying within the range of 10°–40° $2\sigma$. A large proportion of the interplanar distances of TS-1 are tendentially greater than the corresponding distances of pure silicalite, although only slightly, which is in accordance with the larger predictable value of the Ti-O bond distance relative to that of the Si-O bond distance.

Passage from a double reflection to a single reflection is interpreted as a change from a monoclinic symmetry (pseudo orthorhombic) (silicalite) to an effective orthorhombic symmetry, "titanium silicalite" (TS-1). In FIG. 1, the most apparent aforesaid spectral differences are indicated by arrows.

INFRARED EXAMINATION

TS-1 shows a characteristic absorption band at about 950 cm$^{-1}$ (see FIG. 2, spectra B, C and D) which is not present in the pure silicalite spectrum (FIG. 2, spectrum A), and is also absent in titanium oxides (rutile, anastase) and in alkaline titanates.

Spectrum B is that of TS-1 with 5 mol% of $TiO_2$, spectrum C is that of TS-1 with 8 mol% of $TiO_2$, and spectrum D is that of TS-1 with 2.3 mol% of $TiO_2$. As can be seen from FIG. 2, the band intensity at approximately 950 cm$^{-1}$ increases with the quantity of titanium which substitutes the silicon in the silicalite structure.

MORPHOLOGY

From a morphological aspect, TS-1 is in the form of parallelepipeds with chamfered edges. A X-ray microprobe examination has shown that the titanium distribution within the crystal is perfectly uniform, thus confirming that the titanium substitutes the silicon in the silicalite structure, and is not present in other forms.

The process for preparing titanium silicalite comprises the preparation of a reaction mixture consisting of sources of silicon oxide, titanium oxide and possibly an alkaline oxide, a nitrogenated organic base and water, the composition in terms of the molar reagent ratios being as heretofore defined. The silicon oxide source can be a tetraalkylorthosilicate, preferably tetraethylorthosilicate, or simply a silicate in colloidal form, or again a silicate of an alkaline metal, preferably Na or K. The titanium oxide source is a hydrolysable titanium compound preferably chosen from $TiCl_4$, $TiOCl_2$ and $Ti(alkoxy)_4$, preferably $Ti(OC_2H_5)_4$. The organic base is tetraalkylammonium hydroxide, and in particular tetrapropylammonium hydroxide.

The reagent mixture is subjected to hydrothermal treatment in an autoclave at a temperature of between 130° and 200° C. under its own developed pressure, for a time of 6–30 days until the crystals of the TS-1 precursor are formed. These are separated from the mother solution, carefully washed with water and dried. When in the anhydrous state they have the following composition:

$$xTiO_2.(1-x)SiO_2.0.04(RN^+)_2O.$$

The precursor crystals are heated for between 1 and 72 hours in air at 550° C. to completely eliminate the nitrogenated organic base. The final TS-1 has the following composition:

$$xTiO_2.(1-x)SiO_2,$$

where x is as heretofore defined.

Chemical and physical examinations are carried out on the products thus obtained. The alcohol oxidation reaction is conducted at a temperature of between 20° and 100° C., preferably under reflux.

TABLE 1

| | TS - 1 | | | Silicalite[a] | |
|---|---|---|---|---|---|
| 2θ (Cukā) | Interplanar distance d(Å) | Rel. Int.[b] | 2θ (Cukā) | Interplanar distance d(Å) | Rel. Int.[b] |
| 7.94 | 11.14 | vs | 7.94 | 11.14 | vs |
| 8.85 | 9.99 | s | 8.85 | 9.99 | s |
| 9.08 | 9.74 | m | 9.08 | 9.74 | m |
| 13.21 | 6.702 | w | 13.24 | 6.687 | w |
| 13.92 | 6.362 | mw | 13.95 | 6.348 | mw |
| 14.78 | 5.993 | mw | 14.78 | 5.993 | mw |
| 15.55 | 5.698 | w | 15.55 | 5.698 | w* |
| 15.90 | 5.574 | w | 15.90 | 5.574 | w |
| 17.65 | 5.025 | w | 17.65 | 5.025 | w |
| 17.81 | 4.980 | w | 17.83 | 4.975 | w |
| 20.37 | 4.360 | w | 20.39 | 4.355 | w |
| 20.85 | 4.260 | mw | 20.87 | 4.256 | mw |
| 23.07 | 3.855 | s | 23.08 | 3.853 | s |
| | | | 23.28 | 3.821 | ms |
| 23.29 | 3.819 | s | | | |
| | | | 23.37 | 3.806 | ms |
| | | | 23.71 | 3.753 | ms |
| 23.72 | 3.751 | s | | | |
| | | | 23.80 | 3.739 | ms |
| 23.92 | 3.720 | s | 23.94 | 3.717 | s |
| | | | 24.35 | 3.655 | mw |
| 24.41 | 3.646 | m | | | |
| | | | 24.60 | 3.619 | mw |
| | | | 25.84 | 3.448 | w |
| 25.87 | 3.444 | w | | | |
| | | | 25.97 | 3.431 | w |
| 26.87 | 3.318 | w* | 26.95 | 3.308 | w* |
| | | | 29.23 | 3.055 | w |
| 29.27 | 3.051 | mw | | | |
| | | | 29.45 | 3.033 | w |
| 29.90 | 2.988 | mw | 29.90 | 2.988 | mw |
| 30.34 | 2.946 | w | 30.25 | 2.954 | w |
| 45.00 | 2.014 | mw* | 45.05 | 2.012 | mw* |
| 45.49 | 1.994 | mw* | 45.60 | 1.989 | mw* |

[a]Prepared by the method of U.S. Pat. No. 4,061,724; product calcined at 550° C.
[b]vs: very strong; s: strong; ms: medium-strong; m: medium; mw: medium-weak; w: weak; *: multiplet.

The hydrogen peroxide in the aqueous solution is between 10 and 70% w/v. The reaction can be conducted in the absence of solvents if the alcohol is liquid at the reaction temperature, or in the presence of a non-oxidisable solvent. The solvent used can be a polar substance such as tertiary alcohols, ketones, ethers or acids, having a number of carbon atoms which is not too high, and preferably less than or equal to 6. Tert.butanol is the most preferred of the alcohols, and acetone or methyl isobutylketone the most preferred of the ketones. By way of example, alcohols which can be oxidised to aldehydes and/or ketones include benzyl alcohol, 1-heptanol, 1-octanol, isopropyl alcohol, anise alcohol and cyclohexanol.

Some examples illustrating the manner of operating the process according to the invention are given hereinafter, but must not be considered as limitative thereof.

EXAMPLE 1

38 g of acetone, 45.4 g of benzyl alcohol and 2 g of catalyst are fed into a 250 cc three-neck flask fitted with a bulb condenser. When boiling is attained (70° C.), 0.074 moles of aqueous hydrogen peroxide (36% w/v) are added. On termination of the reaction, 7.1 g of benzaldehyde are obtained with an $H_2O_2$ yield of 90.5%. Benzoic acid is not formed.

EXAMPLE 2

Operating as in the preceding example but feeding 3 g of catalyst, 7.4 g of benzaldehyde are obtained with an $H_2O_2$ yield of 94.3%. Benzoic acid is not formed.

EXAMPLE 3

24.16 g of 1-heptanol, 39.48 g of methanol and 3 g of catalyst are fed into a 250 cc three-neck glass flask fitted with a bulb condenser, the operating temperature being 65° C. 4.5 cc of 36% w/v aqueous hydrogen peroxide are added drop by drop. On termination of the reaction, 3.38 g of aldehyde (heptanal) are obtained ($H_2O_2$ yield 61.8%). Heptanoic acid is not formed. It should be noted that the 1-heptanol is selectively oxidised, notwithstanding the fact that methanol alone is oxidisable.

EXAMPLE 4

Operating as in Example 3 but using 39 g of actone instead of methanol (T=60° C.), 4 g of aldehyde are obtained ($H_2O_2$ yield 61.8%). Heptanoic acid is not formed.

EXAMPLE 5

Operating as in Example 4, but using 1-octanol (8.29 g) as substrate and 2 cc of 36% w/v aqueous hydrogen peroxide, 2 g of aldehyde are isolated ($H_2O_2$ yield 74.4%). Octanoic acid is not formed.

EXAMPLE 6

50 cc of methanol (40 g), 20 g of cyclohexanol, 6 cc of 36% w/v aqueous hydrogen peroxide and 3 g of catalyst are fed into a glass autoclave. After 4 hours at 88° C., 95.6% of the fed hydrogen peroxide has reacted. 5.6 g of cyclohexanone are obtained with an $H_2O_2$ yield of 90%.

EXAMPLE 7

About 50 cc of isopropyl alcohol (40 g), 6 cc of 30% w/v aqueous hydrogen peroxide and 3 g of catalyst are fed into a glass autoclave. The operating temperature is 80° C. 3 g of ketone are obtained with a hydrogen peroxide yield exceeding 90%.

EXAMPLE 8

11.15 g of anise alcohol, 39 g of acetone, 2 g of catalyst and 2 cc of 36% w/v aqueous hydrogen peroxide are placed in the glass flask. Operating at 80° C., 3 g of anisaldehyde are obtained ($H_2O_2$ yield 94%).

EXAMPLE 9

45.4 g of benzyl alcohol, 2 g of catalyst and 39 g of acetone are placed in a flask. 25 cc of 10% $H_2O_2$ are added. 7.3 g of benzaldehyde are obtained. The reaction temperature is 65° C.

EXAMPLE 10

Operating as in Example 9 but using 3.5 cc of 69% $H_2O_2$, 7.1 g of benzaldehyde are obtained.

We claim:

1. A process for oxidising primary and/or secondary alcohols to the corresponding aldehyde and/or ketone derivatives, characterised by reacting said alcohols with an aqueous solution of hydrogen peroxide in the presence of synthetic zeolites containing titanium atoms, of the following general formula:

$$xTiO_2 \cdot (1-x)SiO_2$$

where x lies between 0.0001 and 0.04, and possibly in the presence of one or more solvents.

2. A process as claimed in claim 1, characterised in that the oxidation reaction is conducted at a temperature chosen between 20° and 100° C.

3. A process as claimed in claim 1, wherein the hydrogen peroxide is in dilute aqueous solution.

4. A process as claimed in claim 1, wherein the hydrogen peroxide in aqueous solution is between 10 and 70% w/v.

5. A process as claimed in claim 1, wherein the solvent is polar.

6. A process as claimed in claim 5, wherein the polar solvent is chosen from tertiary alcohols, ketones, ethers and acids, having a number of carbon atoms less than or equal to 6.

7. A process as claimed in claim 6, wherein the solvent alcohol is tert.butanol.

8. A process as claimed in claim 6, wherein the solvent ketone is acetone or methylisobutylketone.

9. A process as claimed in claim 1, wherein the alcohols to be oxidised are chosen from benzyl alcohol, 1-heptanol, 1-octanol, isopropyl alcohol and anise alcohol.

10. A process as claimed in claim 1, wherein the reaction is conducted in the absence of solvents if the substrate is liquid at the reaction temperature.

* * * * *